United States Patent [19]

Herslöf et al.

[11] Patent Number: 5,550,263
[45] Date of Patent: Aug. 27, 1996

[54] X-RAY CONTRAST AGENT

[75] Inventors: Bengt Herslöf, Stockholm; Kåre Larsson, Bjärred; Stig Bengmark, Lund, all of Sweden

[73] Assignee: Karlshamns LipidTeknik AB, Stockholm, Sweden

[21] Appl. No.: 157,048

[22] PCT Filed: Jun. 3, 1992

[86] PCT No.: PCT/SE92/00374

§ 371 Date: Dec. 30, 1993

§ 102(e) Date: Dec. 30, 1993

[87] PCT Pub. No.: WO92/21384

PCT Pub. Date: Dec. 10, 1992

[30] Foreign Application Priority Data

Jun. 3, 1991 [SE] Sweden ................................ 9101709

[51] Int. Cl.$^6$ .............................. A61K 49/04; C07F 9/10
[52] U.S. Cl. .................... 554/78; 424/9.455; 424/9.45; 436/508
[58] Field of Search ................... 554/78; 424/5; 436/508

[56] References Cited

U.S. PATENT DOCUMENTS

| | | | |
|---|---|---|---|
| 4,192,859 | 3/1980 | Mackaness et al. ................ | 424/5 |
| 4,235,792 | 11/1980 | Hsia et al. ........................... | 260/403 |
| 4,386,078 | 5/1983 | Horrocks et al. ................... | 514/49 |
| 4,480,041 | 10/1984 | Myles et al. ........................ | 436/508 |
| 4,624,919 | 11/1986 | Kokusho et al. ................... | 435/74 |
| 4,900,680 | 2/1990 | Miyazana et al. .................. | 436/71 |
| 4,921,951 | 5/1990 | Shuto et al. ........................ | 536/26.5 |

FOREIGN PATENT DOCUMENTS

| | | |
|---|---|---|
| 0307175A2 | 3/1989 | European Pat. Off. . |
| 2935195A1 | 4/1980 | Germany . |
| WO88/09165 | 12/1988 | WIPO . |

OTHER PUBLICATIONS

C. Grant, et al., "A Liposomal MRI Contrast Agent: Phosphatidylethanolamine–DPTA," *Magnetic Resonance in Medicine*, 11, pp. 236–243 (Jul. 1989).

J. Weichert, et al., "Potential Tumor–or Organ–Imaging Agents, 26. Polyiodinated 2–Substituted Triacylglycerols as Hepatographic Agents," *J. Med. Chem.* 29, pp. 1674–1682 (Mar. 1986).

J. Weichert, et al., "Potential Tumor–or–Organ–Imaging Agents. 27. Polyiodinated 1,3–Disubstituted and 1,2,3,–Trisubstituted Triacylglycerols," *J. Med. Chem.*, 29, pp. 2457–2465 (May, 1986).

J. Langone, ed., "Immunochemical Techniques," *Methods in Enzymology*, 74, Part C, Academic Press, pp. 152–161 (Jul. 1981).

Primary Examiner—Arthur C. Prescott
Attorney, Agent, or Firm—Hoffmann & Baron

[57] ABSTRACT

The present invention refers to a phospholipid-based compound, that is a phospholipid to which an X-ray contrast-giving moiety has been covalently linked, liposomes comprising said compound as well as the use of said liposomes as a diagnostic or contrast agent.

31 Claims, 1 Drawing Sheet

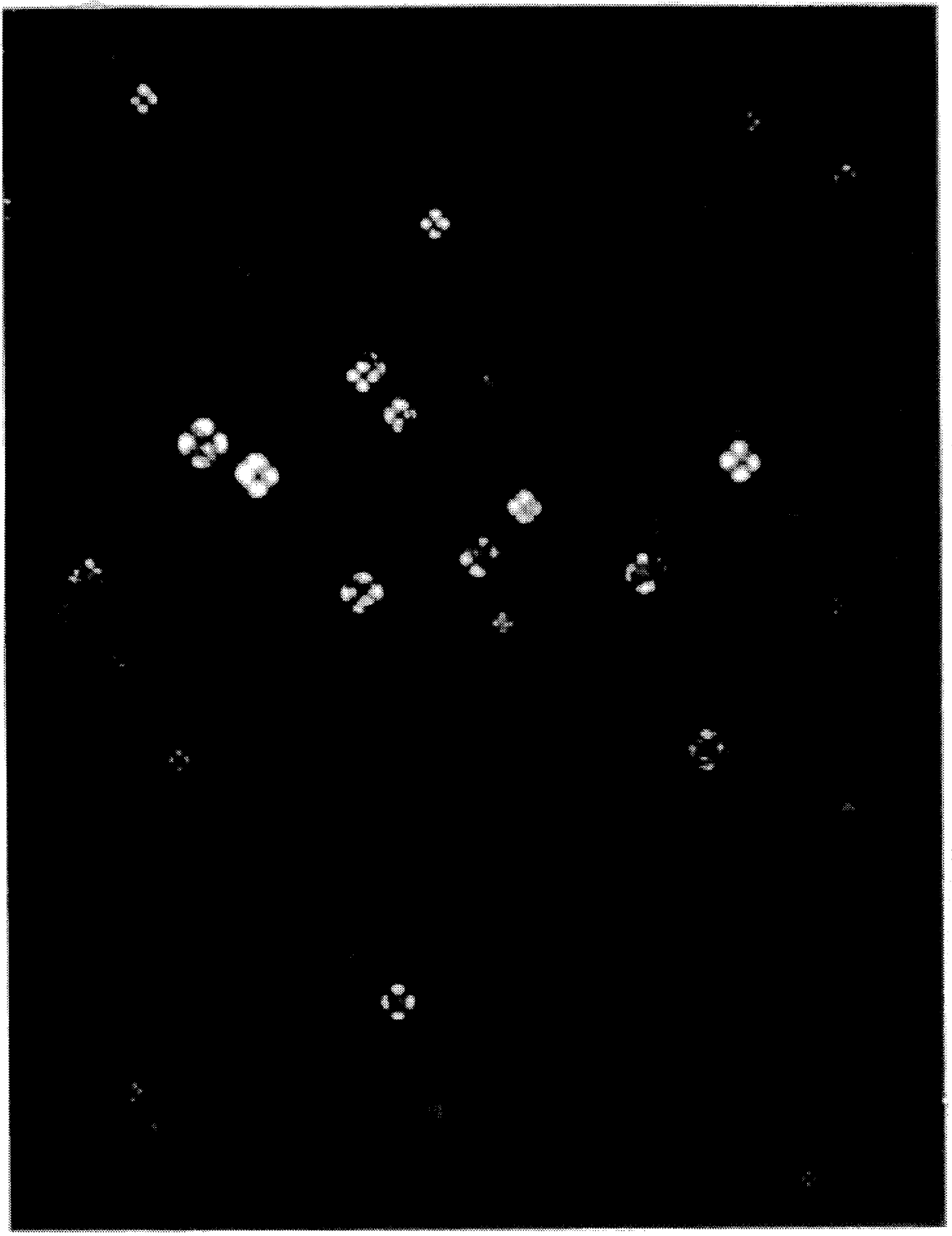

X-RAY CONTRAST AGENT

TECHNICAL FIELD

The present invention is related to a phospholipid-based compound comprising an X-ray contrast-giving moiety, which compound in the form of liposomes in an aqueous formulation after intravenous administration can be used for X-ray examination of the reticuloendothelial system (RES), especially the liver.

BACKGROUND

There is in medicine a great need for a non-toxic contrast agent for the liver. In the liver, as well as in the spleen which are part of the reticuloendothelial system, there are so called Kupffer cells, the normal task of which is to clear the blood of foreign particles. It is a well known fact that colloidal particles, such as liposomes, when injected into the body, are concentrated in said Kupffer cells. In a number of diseases, such as cancer, there are, however, no such cells in the disordered tissue. By using a particulate contrast agent, which will only be taken up by the healthy tissue, there is therefore a possibility to differentiate between disordered and healthy tissue.

In order to replace Thorotrast, which was introduced in 1929 and abandoned due to the development of histological changes, many attemps have been made to find a contrast agent for the liver not being toxic. All these experiments have in common that the results often were diagnostically satisfactory but nevertheless discouraging as all efforts lead to unavoidable toxicity. A number of particulate contrast agents has been developed and tested which have been based on polymeric materials or on lipids combined with a contrast giving substance. Said contrast agents have been of different types such as iodinated compounds for use in X-ray diagnostics, conventional as well as for computed tomography (CT), magnetic materials for use in magnetic resonance imaging (MRI) and radioactive isotopes.

For toxicological reasons, that is for avoiding the risk of radiation as well as of introducing foreign substances, it should be of advantage to use a conventional X-ray contrast agent of the type iodinated carboxylic acid which is well known and highly compatible with the human body.

As there are only about 1% Kupffer cells in the liver, the contrast-giving moiety of the contrast agent must not be too small; it has been concluded that in general the contrast-giving moiety should not be less than about 25% w/w for an uptake to be diagnostically detectable. In addition the size of the particles should be within the interval 0.05–5 μm as larger particles to a great extent are caught in the lungs and smaller particles will not be taken up by the Kupffer cells.

Another problem with a particulate contrast agent to be used for parenteral administration, and intravenous administration in particular, is the demand for sterilization. When a contrast agent is to be prepared on a large scale for a medical application, one of the most important steps in the manufacturing process is the sterilization. In order to remove small viruses and pathogenetic materials heat sterilization is still the only reliable method. The particle structure of many of the previously known particulate carriers for contrast agents, such as liposomes and starch-based particles, can generally not withstand this treatment.

PRIOR ART

Particulate contrast agents based on lipids can be divided into two main categories. On the one hand an appropriate contrast agent can be included in a carrier particle, for instance a liposome, and on the other hand the contrast agent can be linked to a lipid as such, and subsequently by means of excipients be formed to particles, such as liposomes or emulsion droplets. In this context liposome refers to a spherical particle comprising two or more bilayers of mainly phospholipids, in the interspace of which hydrophilic substances, for instance water, can be included. Emulsion refers to drops of lipid, mainly consisting of triglycerides which have been stabilised preferably with phospholipids, in an aqueous continuous phase.

Different methods have been tested in the preparation of lipid systems based on emulsions. Lipoidal® UF (Laboratoire Guerbert, Aulnay-sous-Bois, France) is an iodinated ethyl ester of fatty acids, which has been emulsified and used as a particulate system.

EP-A1-294 534 refers to an X-ray contrast agent emulsion for parenteral, especially intravenous administration, containing iodinated lipids, such as triglycerides or alkyl esters of fatty acids, emulsified in an aqueous phase to which has been added a stability increasing agent and optionally an oil or a fat. This emulsion is based on the Intralipid® concept; lipid emulsions which have been used in clinic as nutrition solutions for many years. The emulsion mainly consists of triglycerides from soybean oil and phospholipids from eggs, which have been emulsified to a stable emulsion having a very low toxicity.

Iodinated alkyl compounds have, however, under certain conditions proved to function as alkylating agents in vivo and also to bring about macrophage activation. This is not surprising as it could be expected that iodinated acyl chains in the cell membrane should lead to changes affecting general membrane functions such as fluidity etc., which in turn have regulating functions. It could therefore be concluded that iodinated lipids should not contain iodine in the hydrocarbon chain.

DE 29 35 195 refers to an X-ray contrast agent for the liver and spleen, which consists of an iodine containing X-ray contrast giving compound of the type 2,4,6-triiodobenzoic acid derivative enclosed in spherical phospholipids, that is liposomes having a multilayer structure.

U.S. Pat. No. 4,192,859 also refers to X-ray contrast media comprising an X-ray contrast agent and a liposome as a carrier therefor. The liposome comprises lecithin and a sterol and is said to include cavities containing the contrast agent therein, i.e. the contrast agent is not chemically bonded to the liposome.

WO 88/09165 refers to an injectable aqueous composition, developed for opacifying organs for X-ray examination, which comprises at least one iodinated organic compound opaque to X-rays encapsulated in liposomic vesicles. It is stated that the particle size of the liposome vesicles should be 0.15–3 μm and the ratio encapsulated iodine to lipids in the liposomic vesicles from 1.5 to 6 g/g.

A general disadvantage with the references cited above referring to liposomes as carriers for contrast agents is that the substances entrapped by the bilayer membranes leak in tissue fluids. This bilayer membrane leakiness also prevents the liposome carriers from being heat sterilizable. There is consequently a need for contrast giving moieties that remain associated to the carrier particle, for instance a liposome, in the body.

Another difficulty with the liposome systems cited above is that the techniques for producing the final dispersion often are complicated and involves stability problems.

DISCLOSURE OF THE INVENTION

The object of the invention is to provide a non-toxic X-ray contrast agent for the reticuloendothelial system which after intravenous administration gives a satisfactory visualization of the liver, and in addition is sufficiently stable to be easy to manufacture and sterilize.

The phospholipid-based compound

The present invention refers to a new phospholipid-based compound, to be precise a phospholipid to which an X-ray contrast-giving moiety has been covalently linked.

The phospholipid based compound of the invention can be represented by the following formula

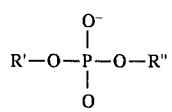

wherein R' is the lipid part of the phospholipid and R" is the contrast-giving moiety of the compound, which has been associated to the phospholipid by a covalent coupling, preferably by an amide or ester bond.

The phospholipids according to the invention are composed of polar and non-polar groups on a backbone molecule, generally glycerol. Also other backbone molecules can be used, for instance the natural sphingosine bases and sterols. Similar structures can also be synthesized from natural or synthetic alcohols and amines. According to a preferred aspect of the invention the phospholipids should be of natural origin, preferably membrane phospholipids.

Glycerophospholipids, that is phospholipids having a glycerol backbone, can be represented by the formula II

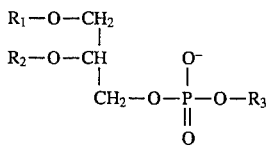

wherein $R_1$ and $R_2$ independently represent $R_4$ or $OCR_4$, wherein $R_4$ represents a saturated or unsaturated, branched or straight chain alkyl or alkylene group having 7–23 carbon atoms, preferably 11–19 carbon atoms; and $R_3$ represents an amide or ester bonding group.

$R_1$ and $R_2$ generally are fatty acid residues of variable length. As preferred examples of fatty acids can be mentioned naturally occuring fatty acids, such as the saturated acids palmitic ($C_{15}H_{31}CO$) and stearic ($C_{17}H_{35}CO$) acid; the monosaturated acid oleic acid ($C_{17}H_{33}CO$); and the polyunsaturated acids linoleic acid ($C_{17}H_{31}CO$) and linolenic acid ($C_{17}H_{29}CO$).

When a phospholipid of natural origin is chosen the acyl chains will be varying with respect to length and number of double bonds in contrast to a phospholipid of synthetic origin, in which case it will be possible to prepare the phospholipid with specific acyl chains. As an example of this can be mentioned that for instance phosphatidylethanolamine (PE) from soybean and egg respectively, have the fatty acid pattern according to Table 1, whereas a synthetic PE can consist of up to 100% C 16:0.

TABLE 1

| Fatty Acid | % by weight soybean PE | % by weight egg PE |
|---|---|---|
| 16:0 palmitate | 21 | 15 |
| 18:0 stearate | 1 | 28 |
| 18:1 (n-9) oleate | 7 | 20 |
| 18:1 (n-7) | 1 | 1 |
| 18:2 linoleate | 63 | 9 |
| 18:3 linolenate | 6 | — |
| 20:4 | — | 10 |
| 20:6 | — | 13 |
| miscellaneous | 1 | 5 |

$R_3$ in the formula II can be represented by $C_1$–$C_5$ alkylene, which may be substituted or not, having a terminal $NH_2$ or OH group, preferably a $C_1$–$C_2$ alkylene amino group, optionally substituted by a hydroxymethyl or carboxymethyl group. As examples can be mentioned the ethanolamine or serine residues, which both have terminal $NH_2$ groups suitable for coupling of the contrast-giving substituent. Said residues are both important consituents of cell membranes in mammals. Examples of other groups are residues from other amino acids; for instance tyrosine and threonine having terminal OH groups in the structure in the same way as serine, which can be associated with the phosphate group. For the man skilled in the art it will be easy to amend this type of group in accordance with the invention.

Sphingophospholipids, such as sphingomyeline analogues, may contain two amino groups and can form two different amides. Sphingophospholipids can be based on different bases, such as sphingosine, sphingenine, sphinganine and hydroxysphinganine.

A preferred class of phospholipids is derived from natural lipids, such as the membrane phospholipids. As examples of glycerophospholipids can be mentioned phosphatidylethanolamine, and phosphatidylserine, as well as phosphatidylinositol and phosphatidylglycerol. The naturally occurring compounds in the class normally have fatty acid residues in the non-polar part of the molecule and are described in the literature (Schmid et al, Progress in Lipid Research 29, 1990, 1). Natural N-acyl phosphatidylethanolamine can e.g. be found in microorganisms, plants (especially cereals), fish and mammals, and thus also in food.

The contrast giving moiety of the phospholipid based compound according to the invention is derived from a conventional iodinated X-ray contrast-giving compound, that is an iodinated carboxylic acid, preferably comprising a triiodo-phenyl group, such as a triiodinated benzoic acid or triiodophenyl propionic acid. Additional iodinated contrast-giving compounds can be found in e.g. Hoey et al, Handb. Exp. Pharmacol, vol 73 (Radiocontrast Agents), 1984, pp 23–125.

The new compounds of the invention of the formula I can be prepared by methods known in the art for chemical coupling of an acid to an amine- or hydroxyterminated compound. Amidation of phosphatidylethanolamine is for instance described by Dawson et al, Biochem. J. 114, 1969, 265.

Preferred phospholipid compounds of the formula I are those swelling in water, a characteristic necessary for the ability to form liposomes spontaneously. For a phospholipid to form a liposome in excess of water it is necessary that a lamellar liquid crystalline phase is formed, as with phosphatidylcholine (PC). Phosphatidylethanolamine (PE) on the other hand normally favours the reversed hexagonal phase.

The compounds of the formula III

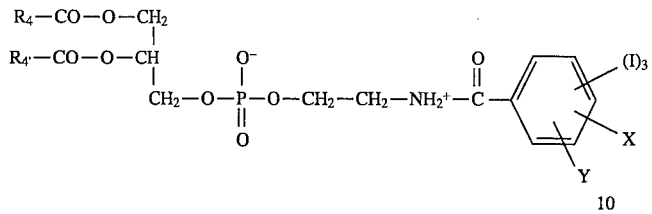

wherein $R_4$ and $R_{4'}$ are defined as above, and X and Y are hydrogen or substituent groups, constitute a preferred class of phospholipid-based compounds of the invention.

Also other associations between the phospholipid and the contrast-giving part of the molecule can easily in a similar way be constructed by the man skilled in the art in order to make combinations which, when broken down in the body, give substances previously known, preferably of natural origin. Such an example is acylornithines and other ornithine lipids.

The phospholipid-based liposomes

The invention also refers to phospholipid-based liposomes, that is multilamellar vesicles, comprising a phospholipid based compound of the formula I above, that is a phospholipid to which an X-ray contrast-giving moiety has been covalently linked.

The liposomes generally are of the size 0.05–10 μm, preferably 0.1–1 μm.

The formation of the liposomes of the compound according to the invention is facilitated by the compound swelling spontaneously in water forming a lamellar liquid crystalline phase having a maximum water content of about 35% by weight. Depending on the compound used and the other conditions a spontaneous formation of liposomes can be obtained when water is added to this lamellar phase. If not, the formation of liposomes can be accomplished by mechanical dispersion of the lamellar liquid-crystalline phase in excess water, whereby the lipid bilayers form closed spherical aggregates, that is liposomes. A preferred method for the dispersion is stirring, for instance by means of an ultraturrax, but shaking, vortexing and rolling can also be performed. If liposomes of a smaller size are aimed at the dispersion could preferably be ultrasonicated.

It should be noticed that the preparation of the liposomes according to the invention does not require any treatment with organic solvents, such as chloroform or dichloromethane, which are used in conventional methods.

If the phospholipid-based compound according to the invention does not swell spontaneously in water, it is possible to obtain liposomes by the addition of a more polar, swellable lipid, preferably phosphatidylcholine.

The liposome formation can be performed at room temperature or any other temperature above 0° C. if the phase transition temperature of the acyl chains (chain melting; gel-to-liquid crystals) is below the freezing point of water, which is the case for natural phospholipids.

To attain a more homogeneous size distribution of the liposomes, the liposomal dispersion can be extruded through a membrane filter.

In a preferred aspect of the invention liposomes can be prepared by direct swelling of the phospholipid-based compound in an aqueous medium without adding any other substances such as stabilizers etc. which are normally required.

A phospholipid-based compound of the formula I, wherein R' is the lipid part of a phosphatidylethanolamine and R" is a derivative of a triiodobenzoyl group, has surprisingly turned out to be able to form liposomes spontaneously in an aqueous medium. This reflects the balanced character of the iodine-containing lipid with respect to hydrophilicitylipophilicity. It could be noticed that "normal" bilayer forming lipids, as for example phophatidylcholine, require mechanical energy in order to be dispersed into liposomes.

A preferred aqueous medium is an isotonic medium, for instance 2.6% w/w glycerol in water, 5% w/w glucose or 10% w/w sucrose. Saline, phosphate buffered saline or any other electrolyte solution should be avoided as dispersion media, as these give rise to the formation of reversed hexagonal liquid crystals.

X-ray contrast agent

The phospholipid-based liposomes of the invention can be used as an X-ray contrast agent. A liposomal dispersion of a concentration of 0.25–20% w/w is non-toxic and sufficiently stable to be heat sterilized. Liposomes having an iodine content of about 32% can be made, which makes them suitable for X-ray diagnostics. By intravenous injection in rabbit, followed by X-ray computed tomography of the liver, a good contrast effect was attained.

A suitable concentration of the liposomal dispersion is 10–20%. As a normal dose of iodine in an liver examination is about 5–15 g/subject, the total dose to be administered will be 80–470 ml.

When the X-ray contrast agent according to the invention is metabolized in vive a water-soluble iodinated substance is formed by enzymatic reaction. This compound is of the same type as the X-ray contrast agents used today of the type triiodobenzoyl derivatives. It is an important aspect of the invention that the phospholipid-based liposomes have been constructed in such a way that, when broken down in the body, previously known substances, preferably of a natural origin, are formed. In general they are decomposed by the action of phospholipases, whereby phospholipase D in particular releases the N-acylethanolamine compound from the phosphate group. The released N-acylethanolamine is metabolized by amidases, which are of frequent occurrence e.g. in the liver of mammals.

DESCRIPTION OF THE DRAWING

The FIGURE shows a microphoto pattern in polarized light of 5% w/w iodine-containing phosphatidylethanolamine liposomes according to Example 5 in a magnification of ×100. The spherical patterns with the Malthesian crosses are characteristic features for liposomes.

EXAMPLES

The invention will be further illustrated by the following examples. Example 1 refers to the synthesis of a phospholipid-based compound of the invention, Examples 2–3 to the preparation of liposomes from said compound and Examples 4–6 to physicochemical characterization of said liposomes.

The dispersions of liposomes were heat sterilized and characterized as follows:

Heat sterilization: 2–5 ml of the dispersion was transferred to a glass vial which was sealed with a rubber stopper and an aluminum cap. The dispersion was then heat sterilized at 121° C. for 20 minutes.

Visual appearance: After heat sterilization the liposomal dispersions were characterized visually with respect to aggregation, sedimentation and colour.

Photomicrography: An Olympus CH-2 polarizing microscope, attached to an automatic exposure photomicrographic system with a large format Polaroid camera back, was used. A small amount of the liposomal dispersion was transferred onto a glass slide and covered with a slide cover. The appearance of the sample was then observed between crossed polarizers.

Turbidity measurements: The turbidity, that is the absorbance, before and after heat sterilization was recorded at 600 nm on a Hitachi U-1100 spectrophotometer at ambient temperature. 1 cm cuvette cells were used and no stirring of the dispersion was performed.

Particle size measurements: The mean particle sizes of liposomes before and after heat sterilization were determined by dynamic light scattering measurements using a Zetasizer 4 (Malvern Instruments, England) equipped with an AZ 110 cell. The scattering angle was 90° and the temperature was 25° C. Data are expressed as cumulant z averages.

EXAMPLE 1

N-(2,3,5-triiodobenzoyl)-phosphatidylethanolamine

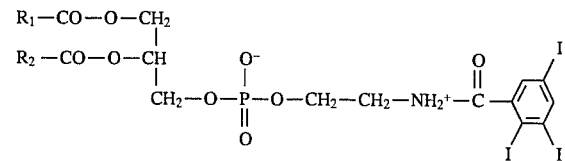

wherein $R_1$ and $R_2$ are 80% $C_{17}H_{31}$ and 20% $C_{15}H_{31}$.

Synthesis: 2.5 g 2,3,5-triiodobenzoic acid is refluxed with 5 ml thionyl chloride for 45 minutes. The excess of thionyl chloride is distilled and the remainder is recrystallized in $CCl_4$. The yield was 2.3 g having a melting point of 90°–91° C.

0.5 g PE, phosphatidylethanolamine from soybeans (Karlshamns Lipidteknik AB) was dissolved in 200 ml chloroform, 20 ml triethylamine was then added and 0.8 g redistilled 2,3,5-triiodobenzoyl chloride. The reaction mixture was stirred for 24 hours at ambient temperature and the reaction was followed by thin-layer chromatography until completion. The reaction mixture was washed carefully with a saturated solution of sodium bicarbonate. The chloroform phase was dried over $MgSO_4$ and was evaporated. The resulting product was recrystallized in hexane. The yield of the final product was 75% with a purity higher than 99.5% (determined by HPLC). The structure of the final compound was confirmed by $^{13}$C-NMR ($CDCl_3$, TMS, 101 MHz); 173.33 and 172.93 (C=O esters), 168.29 (C=O amid); 151.12 ($C_1$ in aromatic ring), 147.3 ($C_5$ in aromatic ring), 135.40 ($C_6$ in aromatic ring), 130.27/130.04/128.17/127.98 (unsaturation in aliphatic chain), 112.10 ($C_4$ in aromatic ring); 106.55 ($C_3$ in aromatic ring); 93.93 ($C_2$ in aromatic ring); 70.53 (CHO glycerol); 64.02 ($CH_2OP$ glycerol); 62.68 ($CH_2O$ glycerol); 45.86 ($POCH_2$); 41.7 ($CH_2N$); 34.34–14.01 (aliphatic chain).

EXAMPLE 2

150 g of the compound of Example 1 was mixed with 850 g 2.6% w/w glycerol in distilled water. The mixture was equilibrated for two hours without stirring in order to swell the lipid. The swollen lipid was then stirred to homogeneity and sterilized by heating at 95° C. for five minutes, followed by aseptic packaging in glass ampoules.

EXAMPLE 3

100 g of the compound of Example 1 was mixed with 900 g distilled water to which 2.6% w/w glycerol had been added in order to achieve an isotonic solution. The lipid was allowed to swell in the aqueous phase for two hours. The mixture was homogenized by ultrasonication. 5 ml of the resulting dispersion was sealed in glass ampoules and heat sterilized in boiling water for five minutes.

EXAMPLE 4

70 mg of the compound of Example 1 was mixed with 6.93 g membrane-filtered water. The mixture was allowed to swell for 2 h during slow agitation which resulted in a homogeneous dispersion.

One part of the dispersion was filtered through a 0.45 μm membrane-filter (A). Another part of the dispersion was filtrated through a 0.45 μm membrane filter, followed by heat sterilization (B). The last part was untreated (C).

The turbidity was then measured and the following results were obtained:

| Sample | Turbidity/Absorbance units |
| --- | --- |
| A | 0.657 |
| B | 0.652 |
| C | 0.780 |

The cuvette cells were left to stand at ambient temperature for 1 month. No appreciable sedimentation could be observed after visual examination.

EXAMPLE 5

3.03 g of the compound of Example 1 was mixed with 11.79 g membrane-filtered water och 0.38 g 99.5% glycerol. The mixture was allowed to swell overnight during slow agitation. A part of the resulting homogeneous dispersion was diluted with 2.50% w/w glycerol in water to give a final lipid concentration of 5.00% w/w.

EXAMPLE 6

The dispersion of Example 5 was diluted with 2.6% w/w glycerol in water to give a concentration of 0.25% w/w and was filtered through a 0.45 μm polycarbonate membrane filter in order to remove dust particles. One part of the dispersion was heat sterilized (A) whereas another part was untreated (8). The size distributions of the samples were then measured.

| Sample | Average particle size, nm |
|---|---|
| A | 184 |
| B | 199 |

The results clearly show that the liposomes according to the invention were more or less unaffected by the heat sterilization, i.e. the liposomal structure was maintained without aggregation and subsequent sedimentation. In general the size of the particles was somewhat reduced after the heat treatment. Furthermore, the fraction of particles larger than 1000 nm was reduced from being ca. 5% of the total particles to less than 0.1% after heat sterilization.

Biological test

In order to evaluate the efficiency of the new iodine-containing phospholipid based liposomes as a liver-specific contrast medium at X-ray computed tomography, studies were performed in rabbits. Scans were obtained immediately prior to and 30 minutes after intraveneous injection of the dispersion (containing 50 mg iodine per ml solution). The concentration in the rabbit was approximately 50 mg iodine per kg body weight. The injection rate was 20 ml per minute. The average increase in attenuation was 34.5 Hounsfield units (HU), which is 3 times higher than what was found by Ivancek when Intraiodole was used in approximately the same concentration, and in level with what was achieved with Intraiodole containing 300% more of iodine (Acta Radiologica 30, 1989, 409).

TABLE 2

| | Attenuation in rabbit, in HU | |
|---|---|---|
| | 0 | 30 min |
| Region of interest | 55.3 | 92.2 |
| (circular) | 47.1 | 86.2 |
| | 56.1 | 89.9 |
| | 58.2 | 79.7 |
| | 45.4 | 77.6 |
| | 43.0 | 82.1 |
| | 42.6 | 86.0 |
| | 50.6 | 82.8 |
| | 46.6 | 80.9 |
| | 47.1 | 82.8 |
| | | 79.9 |
| | | 84.7 |
| Mean value ± standard deviation | 49,2 ± 1,76 | 83,7 ± 1,24 |

The above data show that there is an increase of the attenuation of 34.5 HU 30 minutes after the administration, which is a satisfactory increase for assessing liver tumors.

We claim:

1. A phospholipid-based compound which comprises a phospholipid to which an x-ray contrast-giving moiety has been covalently linked by means of an ester or an amide bond.

2. The compound according to claim 1 in which said phospholipid comprises a terminal amino group, to which the x-ray contrast-giving moiety has been linked by means of an amide bond.

3. The compound according to claim 1 in which said phospholipid is a glycerophospholipid.

4. The compound according to claim 3 wherein said glycerophospholipid is selected from the group consisting of phosphotidylethanolamine, phosphotidylserine, phosphotidylinositol and phosphotidyglycerol.

5. The compound according to claim 1 in which said x-ray contrast-giving moiety is an iodinated carboxylic acid.

6. The compound according to claim 5 in which said iodinated carboxylic acid is selected from the group consisting of triiodinated benzoic acid and triiodophenyl propionic acid.

7. A compound according to claim 1 wherein said phospholipid-based compound swells spontaneously in an isotonic aqueous solution.

8. Phospholipid-based liposomes comprising the phospholipid-based compound of claim 1.

9. The phospholipid-based liposomes of claim 8 which are dispersed in an aqueous environment.

10. Liposomes as claimed in claim 8 which are formed without addition of excipients.

11. Liposomes as claimed in claim 8 which are of the size 0.05–10 μm.

12. Liposomes as claimed in claim 11 which are of the size 0.1–1 μm.

13. A method of preparing an x-ray contrast agent which comprises covalently linking an x-ray contrast-giving moiety to a phospholipid by means of an ester or an amide bond.

14. The method of claim 13 wherein said phospholipid comprises a terminal amino group, to which the x-ray contrast-giving moiety has been linked by means of an amide bond.

15. The method of claim 13 wherein said phospholipid is a glycerophospholipid.

16. The method of claim 15 wherein said glycerophospholipid is selected from the group consisting of phosphotidylethanolamine, phosphotidylserine, phosphotidylinositol and phosphotidylglycerol.

17. The method of claim 13 wherein said x-ray contrast-giving moiety is an iodinated carboxylic acid.

18. The method of claim 17 wherein said iodinated carboxylic acid is selected from the group consisting of triiodinated benzoic acid and triiodophenyl propionic acid.

19. The method of claim 13 wherein said phospholipid-based compound swells spontaneously in an isotonic aqueous solution.

20. Method of providing a non-toxic x-ray contrast agent for x-ray diagnosis comprising:
    administering to a host a phospholipid-based compound comprising a phospholipid to which the x-ray contrast giving moiety has been linked by means of an amide bond to a terminal amino group of said phospholipid.

21. The method of claim 20 wherein said phospholipid is a glycerophospholipid.

22. The method of claim 21 wherein said glycerophospholipid is selected from the group consisting of phosphotidylethanolamine, phosphotidylserine, phosphotidylinositol and pholsphtidylglycerol.

23. The method of claim 20 wherein said x-ray contrast-giving moiety covalently linked to said phospholipid is an iodinated carboxylic acid.

24. The method of claim 23 wherein said iodinated carboxylic acid is selected from the group consisting of triiodinated benzoic acid and triiodophenylpropionic acid.

25. The method of claim 20 wherein said phospholipid-based compound swells spontaneously in an isotonic aqueous solution.

26. The method of claim 13 further comprising forming phospholipid-based liposomes which comprise the compound resulting from said linking.

27. The method of claim 26 wherein said liposomes are dispersed in an aqueous environment.

28. The method of claim 26 wherein said liposomes are formed without addition of excipients.

29. The method of claim 26 wherein said liposomes are of the size 0.05–10 μm.

30. The method of claim 29 wherein said liposomes are of the size 0.1–1 μm.

31. The method of claim 20 wherein said diagnosis comprises visualizing the reticuloendothelial system.

* * * * *